United States Patent [19]

Hiller et al.

[11] Patent Number: 5,215,556
[45] Date of Patent: Jun. 1, 1993

[54] APPARATUS AND METHOD FOR ESTABLISHING A TEMPERATURE GRADIENT IN A CHROMATOGRAPHY COLUMN

[75] Inventors: Joseph F. Hiller; Glen H. Hughes; Daniel P. Martin, all of Midland, Mich.

[73] Assignee: The Dow Chemical Company, Midland, Mich.

[21] Appl. No.: 868,917

[22] Filed: Apr. 15, 1992

[51] Int. Cl.$^5$ .......................................... B01D 15/08
[52] U.S. Cl. .......................................... 55/67; 55/197; 55/208; 55/386
[58] Field of Search .................. 55/67, 197, 208, 386; 73/23.25, 23.26

[56] References Cited

U.S. PATENT DOCUMENTS

| | | | |
|---|---|---|---|
| 2,377,900 | 6/1945 | Podbielniak | 73/23.26 |
| 3,035,383 | 5/1962 | Sanford et al. | 55/208 X |
| 3,043,127 | 7/1962 | DeFord et al. | 55/67 X |
| 3,057,183 | 10/1962 | DeFord | 55/197 X |
| 3,146,616 | 9/1964 | Loyd | 55/67 X |
| 3,152,470 | 10/1964 | Reinecke et al. | 55/67 X |
| 3,225,520 | 12/1965 | Burow | 55/197 X |
| 3,225,521 | 12/1965 | Burow | 55/197 X |
| 3,309,504 | 3/1967 | Rosso et al. | 73/23.25 X |
| 3,440,397 | 4/1969 | Vesper et al. | 73/23.25 X |
| 3,449,938 | 6/1969 | Giddings | 55/67 X |
| 3,926,800 | 12/1975 | Stephens | 55/208 X |
| 4,004,881 | 1/1977 | Ligon, Jr. | 73/23.25 |
| 4,484,061 | 11/1984 | Zelinka et al. | 73/23.25 X |
| 4,872,334 | 10/1989 | Watanabe | 73/23.25 X |
| 4,923,486 | 5/1990 | Rubey | 55/197 X |
| 5,028,243 | 7/1991 | Rubey | 55/197 X |
| 5,114,439 | 5/1992 | Yast et al. | 55/197 X |

OTHER PUBLICATIONS

Gas-Liquid Chromathermography, Analytical Chemistry, vol. 32, No. 3, Mar. 1960, pp. 436-437 A. Glenn Nerheim.

Temperature Gradients in Gas Chromatography, Journal of Chromatography, 373 (1986) 21-44, V. G. Berezkin et al.

Primary Examiner—Robert Spitzer
Attorney, Agent, or Firm—Ronald J. Snyder; Timothy S. Stevens

[57] ABSTRACT

Apparatus and method for temperature gradient capillary gas chromatography wherein the chromatography column is surrounded by an inner tube and the inner tube is surrounded by an outer tube. A first heat transfer fluid is heated to a first temperature and is flowed between the inner tube and the column in the same direction as the flow of carrier gas through the capillary column. A second heat transfer fluid is heated to a second temperature and is flowed in the opposite direction between the outer tube and the inner tube, the second temperature being lower than the first temperature. The invention is also an improved capillary gas chromatography method of the type that generally includes the steps of flowing a carrier gas through a capillary gas chromatography column to a detector, introducing a sample to be analyzed into the column and then detecting chromatographically resolved components of interest of the sample, the method having an optimum carrier gas velocity through the column, wherein the improvement of the instant invention is to establish a negative temperature gradient along at least a portion of the longitudinal length of the capillary gas chromatography column and to flow the carrier gas through the capillary gas chromatography column at less than the optimum carrier gas velocity.

20 Claims, 6 Drawing Sheets

APPARATUS AND METHOD FOR ESTABLISHING A TEMPERATURE GRADIENT IN A CHROMATOGRAPHY COLUMN

TECHNICAL FIELD

This invention relates to an apparatus and method for improving chromatographic analysis, especially in the field of capillary gas chromatography.

BACKGROUND OF THE INVENTION

Chromatography is a well known separation technique whereby a number of analytes contained in a sample solution can be separated from one another. By using a suitable detector, the identity and amount of each analyte in the sample solution can be estimated.

One of the most useful forms of chromatography used for analytical purposes is gas chromatography, and particularly capillary gas chromatography. The sorbent material, or stationary phase, in this method can be a liquid or crosslinked polymer coated on the inner walls of the capillary column. An inert carrier gas such as helium is flowed through the column and a small amount of the sample solution is simultaneously vaporized and injected into the carrier gas ahead of the column. Once the sample is within the capillary column, the components of the sample are ideally separated into individual bands which move at different rates down the length of the column.

The mechanism by which this separation occurs is in general a continuous series of absorption and extraction steps. A component in the sample is absorbed into the stationary phase, and thereafter extracted into the carrier gas, or mobile phase, as it passes over the stationary phase. At any point in the column, the concentration of a component in the stationary phase is in equilibrium with the concentration of the component contained in the mobile phase. These two concentrations are related to one another by what is known as the partition coefficient (k), which is the concentration of a component in the stationary phase divided by the concentration of the component in the mobile phase. In this fashion, a moving band of the component is created, and since the partition coefficient for each component is ideally unique, each component contained in the sample will move at a different rate through the column.

The identity and amount of each component present in the sample can be determined by the detector, which is usually attached to a recording device which produces a plot (chromatogram) having separate peaks for each component in the sample. By comparing the length of time it takes for a component to pass through the column (the retention time) with standardized data for similar column conditions, one can estimate the identity of the component. The concentration of each component is normally determined by comparing the area beneath each component peak with the area beneath a standard peak of the component.

The partition coefficients are also influenced by the temperature of the column itself. Usually as the temperature increases, the partition coefficient correspondingly decreases, which in turn results in the component bands moving at a faster rate through the column. Due to this phenomenon, the temperature of the column can be tailored for the sample solution being analyzed. On the other hand, however, the column temperature suitable for resolving several components in a sample may not be a suitable temperature for resolving other components in the sample. At one temperature, for example, several components in a mixture, particularly the more volatile ones, may move through the column at a rate close to that of the carrier gas itself. The chromatogram peaks for such components will often overlap one another. At the same time, other components may move so slowly through the column that the analysis period is too long and/or the component bands spread or diffuse to an unacceptable width.

One means for addressing these problems is to use temperature programming, whereby the temperature of the entire column is increased in a controlled manner while the sample solution is passing through the column. By this method, the faster moving component bands can often be resolved from one another at a relatively low column temperature and then the component bands which typically move at a slower rate through the column are speeded up by increasing the column temperature. Temperature programming is usually accomplished by placing the entire column inside an oven whose temperature can be controlled.

Even with temperature programming, however, some sample mixtures cannot be properly analyzed due to overlapping component peaks, band dispersion, or a combination of both. In addition, another drawback of temperature programming is that the oven must be recycled back to its initial temperature before each subsequent sample can be run through the column, thereby limiting the number of samples that can be run in a given period.

An alternative arrangement that has been discussed in the literature is the use of temperature gradients, or chromathermography, as some have referred to it. In this approach, the temperature within the column varies along its length from a relatively high temperature at the inlet of the column to a relatively lower temperature at the outlet of the column, i.e., a negative temperature gradient. An additional modification of this method, is where the column temperature also varies with time, thereby producing a tim-variable temperature gradient along the length of the column, e.g., a beginning gradient of from 150° C. at the column inlet to 50° C. at the column outlet and a final gradient of from 250° C. at the column inlet to 100° C. at the column outlet. While both of these approaches have been discussed in the literature, heretofore there has not been an accepted way of generally applying these techniques to capillary columns.

By applying a negative temperature gradient along the length of the column all of the components can be moved through the column more quickly, while at the same time the resolution between chromatogram peaks is often improved, and band spreading or diffusion is often decreased. Even better results can be obtained when the temperature gradient varies with time.

While time-variant temperature gradient chromatography has previously been attempted, the methods and devices used to achieve this effect were not accepted for commercial use. Nerheim, in an article entitled "Gas-Liquid Chromathermography," described the use of a motor-driven heater fitted around a gas chromatography column. This device, and similar ones used by others, however, are bulky for everyday use and are not easily applied to long capillary columns (which can often be 60 meters in length or longer). Moreover, these devices are generally incapable of producing a linear temperature gradient in the column.

Another method previously used to establish a time-variable thermal gradient in a column involves painting the outside of the column with varying levels of resistive paint along the length of the column. By applying electric current to the outer layer of the column, a temperature gradient is produced. This thermal gradient can be varied with time by changing the level of current provided to the resistive paint. One problem with this technique, however, is that each column must be separately painted.

A summary of other impractical methods for establishing temperature gradients in capillary columns which have been tried is contained in the article by Berezkin, et al. entitled "Temperature Gradients in Gas Chromatography." FIG. 12 of this article, for example, shows one particular method for applying a time-variable temperature gradient along a chromatography column. The device shown in FIG. 12, however, suffers from the drawback of not easily being capable of producing a linear temperature gradient.

Consequently, heretofore, there has not been available any commercially accepted method and apparatus for establishing a linear, time-variable temperature gradient in a capillary chromatography column.

SUMMARY OF THE INVENTION

While not exclusive, the following describes some of the important features and objectives of the present invention.

It is an object of the present invention to provide a simple apparatus for producing a temperature gradient in a chromatography column.

It is another object of the present invention to provide a simple apparatus for producing a linear, time-variable temperature gradient in a chromatography column.

It is a further object of the present invention to provide an apparatus for establishing a linear, time-variable temperature gradient in a chromatography column, wherein the apparatus can be easily constructed from readily available materials, and further wherein repeatable and consistent results can be obtained from identically configured apparatuses.

It is yet another object of the present invention to provide an apparatus for establishing a time-variable, linear temperature gradient along the length of a chromatography column wherein the apparatus, and therefore the temperature gradient in the column, can be readily acted upon by an automatic control means.

It is a further object of the present invention to provide an apparatus for establishing a time-variable, linear temperature gradient in a chromatography column wherein the chromatography column can be changed without affecting the performance of the apparatus.

It is yet another object of the present invention to provide an apparatus and method for establishing a linear, time-variable temperature gradient in a chromatography column, wherein improved separations can be obtained at carrier gas linear velocities previously thought to be less than optimum.

The foregoing objects can be accomplished, in accordance with one aspect of the invention, by providing a tubular member surrounding and extending along at least a portion of the length of a chromatography column, thereby forming a first annular space between the tubular member and the column, with a heat transfer fluid of controllable temperature and flow rate flowing through the first annular space and an outer tubular member surrounding and extending along the length of the inner tubular member, thereby forming a second annular space between the outer and inner tubular members, and a second heat transfer fluid flowing through the second annular space.

A method aspect of the invention is an improved capillary gas chromatography method of the type that generally includes the steps of flowing a carrier gas through a capillary gas chromatography column to a detector, introducing a sample to be analyzed into the column and then detecting chromatographically resolved components of interest of the sample, the method having an optimum carrier gas velocity through the column, wherein the improvement is to establish a negative temperature gradient along at least a portion of the longitudinal length of the capillary gas chromatography column and to flow the carrier gas through the capillary gas chromatography column at less than the optimum carrier gas velocity. Another aspect of the invention is a method for temperature gradient chromatography that includes two steps. The first step is to moderate the temperature of a chromatographic column with a first heat exchange fluid. The second step is to moderate the temperature of the first heat exchange fluid with a second heat exchange fluid so that a linear temperature gradient is created along the longitudinal length of the chromatographic column.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
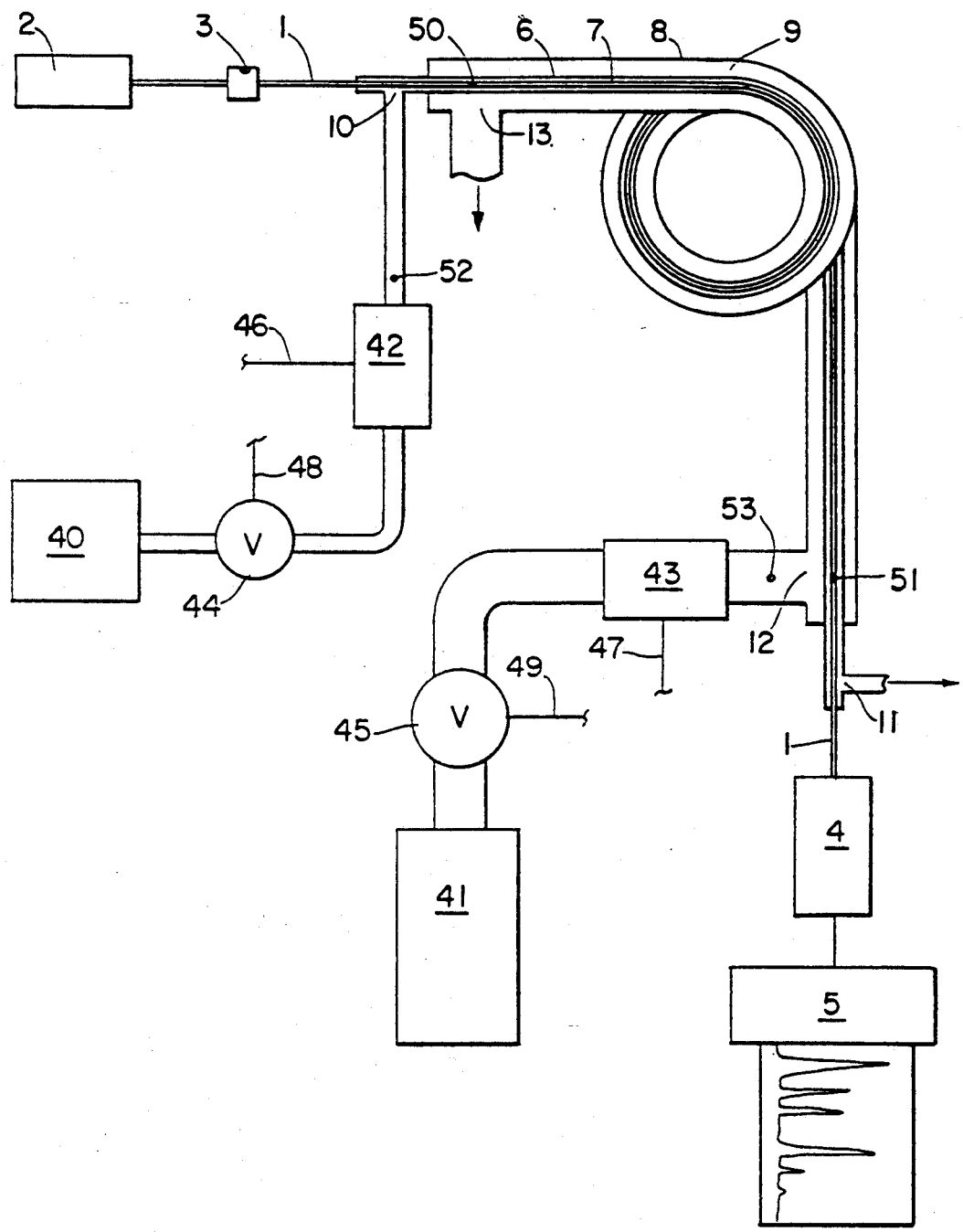
FIG. 1 is a schematic illustration of a preferred embodiment of the apparatus made in accordance with the present invention.

Referring now to the drawings in detail, wherein like numerals indicate the same elements throughout the views, FIG. 1 is a schematic illustration of a preferred embodiment of an apparatus for establishing a linear temperature gradient in a chromatography column, made in accordance with the present invention. Chromatography column 1 is illustrated as a standard capillary column used for gas chromatography. It is contemplated that any type of capillary column can be utilized, and, in fact, the apparatus of the present invention can easily be adapted for use with other types of chromatography, including packed column gas chromatography and liquid chromatography. A capillary column is defined in the invention as a column having an internal diameter of less than one millimeter and containing a chromatographic stationary phase such as a wall coated open tube, a porous layer open tube and a packed tube. Carrier gas source 2, sample injection port 3, detector 4, and chart recorder 5 illustrated can similarly be of any type applicable for gas chromatography. For example, the detector could be of the gas thermal conductivity or flame ionization type. Most preferably, the linear temperature gradient of the invention is perfectly linear. However, it should be understood that in practice a perfectly linear temperature gradient is not likely nor critical in the invention.

The basic technique of the present invention for providing a linear temperature gradient along at least a portion of the length of a chromatography column is to utilize two heat transfer fluids to establish a reasonably linear temperature gradient along at least a portion of the column.

As shown in FIG. 1, an inner tubular member 6 surrounds, and extends along a substantial portion of the longitudinal length of chromatography column 1, thereby forming a first annular space 7 between inner tubular member 6 and column 1. However, the apparatus of the present invention could also be applied to a small portion of the column. Preferably, inner tubular member 6 extends to a position adjacent the column as close to injection port 3 as possible, and, at the other end, extends as close to detector 4 as possible. Inner tubular member 6 can be constructed of any heat conducting material such as stainless steel or copper. For optimal results, however, inner tubular member 6 should be constructed of a material having as high a heat conductance as possible, while still maintaining sufficient structural integrity. One especially preferred material for inner tubular member 6 is aluminum, however copper, of course, could also be utilized. It should be understood that the cross-sectional shape of the inner tubular member 6 is not critical, i.e., it need not be round but can be other shapes such as oval or square.

As further shown in FIG. 1, column 1 and inner tubular member 6 are typically coiled to permit the use of long columns (sometimes greater than 60 meters in length) while minimizing physical space requirements. Thus, it will be understood that inner tubular member 6 and corresponding column 1 do not necessarily have to be coiled if space is not a limiting or practical factor.

An outer tubular member 8 is also provided, and telescopes over and preferably surrounds at least a substantial portion of the longitudinal length of inner tubular member 6, however, if desired, it could encompass only a small portion of inner tubular member 6. In this way outer tubular member 8 forms a second annular space 9 between the two. Preferably, the cross-sectional area of the first annular space 7 is the same as the cross-sectional area of the second annular space 9. While the outer tubular member may be made of any material, including stainless steel or copper, it is preferred that it be constructed of a highly insulating material. One preferred material would be a high temperature polymer such as TEFLON fluoropolymer from DuPont. Alternatively, the outer tubular member 8 can be covered with thermal insulation such as glass fiber insulation. It should be understood that the cross-sectional shape of the outer tubular member 8 is not critical, i.e., it need not be round but can be other shapes such as oval or square.

Attached near respective ends of inner tubular member 6 are a fluid inlet 10 and a fluid outlet 11. In the same fashion, outer tubular member 8 also has a fluid inlet 12 and a fluid outlet 13. The purpose of these fluid inlets and outlets is to permit a heat transfer fluid to be flowed through both the inner and outer tubular members, and any of a number of constructions could be used for these.

Figure 2:
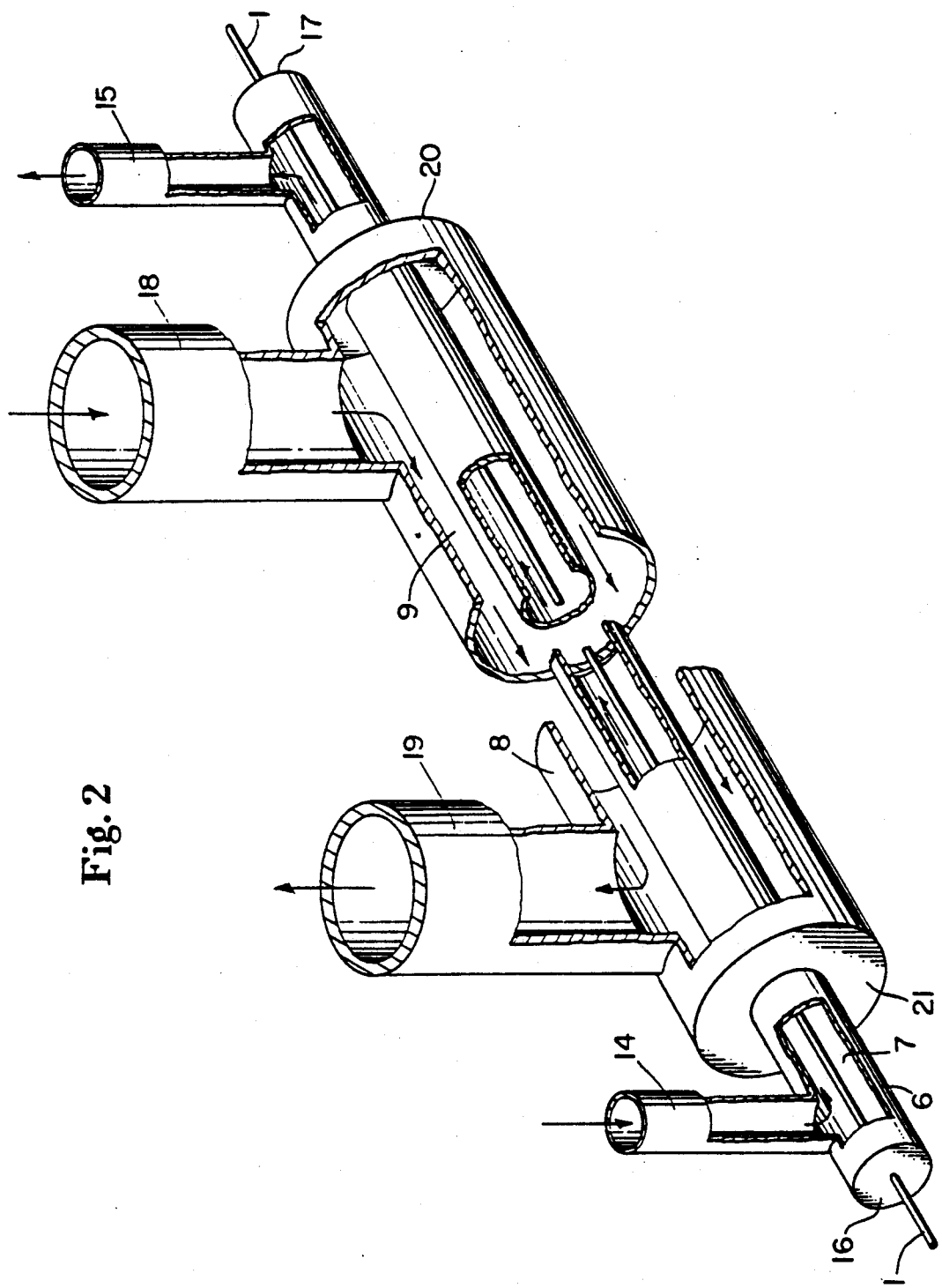
FIG. 2 is a partially broken-out diagrammatic view of a preferred embodiment of the inner and outer tubular members of the present invention, showing countercurrent heat transfer fluid flow.

A preferred embodiment of the respective fluid inlets and outlets is presented in FIG. 2, which is a partially broken-out diagrammatic view of the apparatus. As indicated by the arrows, the flow of the two heat transfer fluids in FIG. 2 is countercurrent to one another. According to the embodiment shown in FIG. 2, the fluid inlet and outlet of inner tubular member 6 are identical passageways, 14 and 15 respectively, extending away from, and in fluid communication with inner tubular member 6. Passageways 14 and 15 may be constructed of any suitable material, and normally would be of the same material as inner tubular member 6. Attachment of passageways 14 and 15 can be accomplished by merely welding them to inner tubular member 6.

As further shown in FIG. 2, the respective ends 16 and 17 of inner tubular member 6 are completely sealed except for an opening on each permitting column 1 to extend from ends 16 and 17. While ends 16 and 17 could simply be plugs welded to inner tubular member 6 and to column 1 in order to form tight seals, it is desired that column 1 be readily changeable without affecting the apparatus. Thus, it is preferred that ends 16 and 17 be threaded caps having front and back ferrules constructed of graphite on each. These ferrules are able to clamp down on column 1 and thus provide a tight seal without damaging column 1. Additionally, since the caps are threaded and not permanently welded, column 1 can be easily removed and replaced without damage.

The fluid inlet and outlet of outer tubular member 8, as shown in FIG. 2, are similar in structure to the inlet and outlet of inner tubular member 6, and are shown as passageways 18 and 19, respectively. Passageways 18 and 19 are welded to outer tubular member 8, and would normally be constructed of a material similar to that of outer tubular member 8.

The respective ends 20 and 21 of outer tubular member 8 are merely end plugs welded to outer tubular member 8, having openings to permit inner tubular member 6 to extend from ends 20 and 21. Unlike ends 16 and 17, however, ends 20 and 21 may be directly welded to inner tubular member 6 in order to form a tight seal, since there is generally no need to be able to remove inner tubular member 6 from outer tubular member 8.

Alternatively, the fluid inlets and outlets on the inner and outer tubular members may comprise tee-type fittings attached to each end of inner and outer tubular members 6 and 8, respectively. By utilizing appropriate reducing ferrules on the fittings, the required seals referred to above may be formed. One type of fitting particularly useful in this alternative embodiment is Swagelok tube fittings (manufactured by the Crawford Fitting Co.).

Returning to FIG. 1, in order to establish a reasonably linear temperature gradient in column 1, means for flowing heat transfer fluids through inner and outer tubular members 6 and 8 must be provided. The means utilized for this purpose will largely be dependent upon the type of heat transfer fluids being employed. The heat transfer fluids can be either gaseous or liquid, and should be selected based upon careful consideration of cost, ease of flowing, desired operating temperatures, heat transfer properties, and other concerns. There is no requirement that the inner and outer heat transfer fluids be identical, or even that they both be a gas or both be a liquid, however normally this will be the case. One preferred heat transfer fluid is air, since it is readily and cheaply available, and its heat transfer properties make it a suitable fluid for most applications. In addition, after use the air may be safely vented to the atmosphere. Preferably, if the cross-sectional area of the first annular space 7 is equal to the cross-sectional area of the second annular space 9, then the flow rates of the heat transfer fluids are equal to each other.

When the heat transfer fluids being employed in the apparatus of FIG. 1 are gaseous, the means for flowing these fluids through the apparatus may simply be pressurized sources of the gas. Thus, pressurized sources of inner and outer heat transfer fluids, 40 and 41 respectively, in fluid communication with inner and outer tubular members 6 and 8 respectively, are provided in FIG. 1. If it is desired that liquid heat transfer fluids be utilized, sources of pressurized fluid 40 and 41 may be replaced by pumps, or some other means for flowing fluids.

If the inlet temperatures of the inner and outer heat transfer fluids flowing through the apparatus of FIG. 1 are not identical, and the fluids are flowing in opposite directions (as shown in greater detail in FIG. 2) a temperature gradient will be established in the column due to the heat transfer that takes place between the two flowing fluids and the column itself. Additionally, it has been found that this temperature gradient can be substantially linear along most of the length of the column, a result which has proven to be quite beneficial.

Since inlet 10 and outlet 11 of inner tubular member 6 are preferably identical structures, and inlet 12 and outlet 13 of outer tubular member 8 are also identical structures, the flow direction of either or both heat transfer fluids can be reversed simply by reorienting their respective flowing means to the opposite end of the corresponding tubular member. Thus, should it be desired to have both the inner and outer heat transfer fluids flowing in the same direction in the apparatus shown in FIG. 1, pressurized source of outer heat transfer fluid 41 can be placed in fluid communication with outer tubular member 8 at outlet 13. This is in contrast to FIG. 1 where pressurized source 41 is shown in fluid communication with outer tubular member 8 at inlet 12, thereby producing the normally desired countercurrent flow.

When a linear temperature gradient is established in the column, the resolution between peaks can be improved if the temperature near the entrance of the column is greater than that near the column exit, i.e., a negative temperature gradient. This is due to the fact that band spreading or diffusion is reduced. As a component band moves through a column having a temperature gradient of negative slope (i.e. progressively cooler along its length), it will be evident that the leading edge of the component band will move at a slower rate than the trailing edge of the band. This in turn causes each band to become compressed, or focused, as it moves down the column, thereby, in theory, improving the resolution between peaks or at least sharpening the peaks. Higher temperatures may also be employed along at least a part of the column, as compared with isothermal operation, thereby greatly reducing the retention times of the components. Additionally, if the temperature gradient is not at least somewhat linear, there may be "flat spots" in the temperature profile where band focusing will not occur, and instead band spreading will ensue.

In order to produce a time-variable, substantially linear temperature gradient in column 1, as opposed to the steady-state temperature gradient described above, a means for controlling the temperature of at least one of, and preferably both heat transfer fluids must be provided. Additionally, it is also preferable to provide a means for controlling the flow rate of at least one of, and preferably both heat transfer heat fluids.

As shown in FIG. 1, one preferred means for controlling the temperature of the inner and outer heat transfer fluids is placing adjustable heaters 42 and 43 in fluid communication with the fluid inlets of tubular members 6 and 8. Other equivalent means for controlling the fluid temperatures may be employed, the structure of which will depend on the type of heat transfer fluids being utilized.

As further shown by FIG. 1, the means for controlling the flow rates of the inner and outer heat transfer fluids are preferably adjustable valves 44 and 45, placed in fluid communication with heaters 42 and 43. As will be evident, however, valves 44 and 45 may be placed anywhere in the path traversed by the heat transfer fluids, and may also be used to completely stop the flow of one or both heat transfer fluids. Once again the type of valve used will depend on the fluids being employed. In the case of gaseous fluids, 44 and 45 may be needle valves to allow for precise controlling of the flow rates.

By allowing the linear temperature gradient in the column to vary with time, the chromatographic analysis being performed can be particularly tailored for the sample being analyzed. In this way separations of improved resolution and speed may be obtained.

It is believed that for each component in a sample there is an ideal column temperature for optimal resolution of that component. By establishing a temperature gradient of negative slope in the column and then "moving" this gradient down the length of the column (i.e., increasing, with time, the temperature of every point in the column) optimal separations can be obtained. In addition, the retention time for the components can be reduced since the temperature is increasing. At the same time, the identical band narrowing that is obtained with a steady-state temperature gradient will occur. Thus, optimal resolution of peaks and speed of analysis can be obtained.

Figure 3:
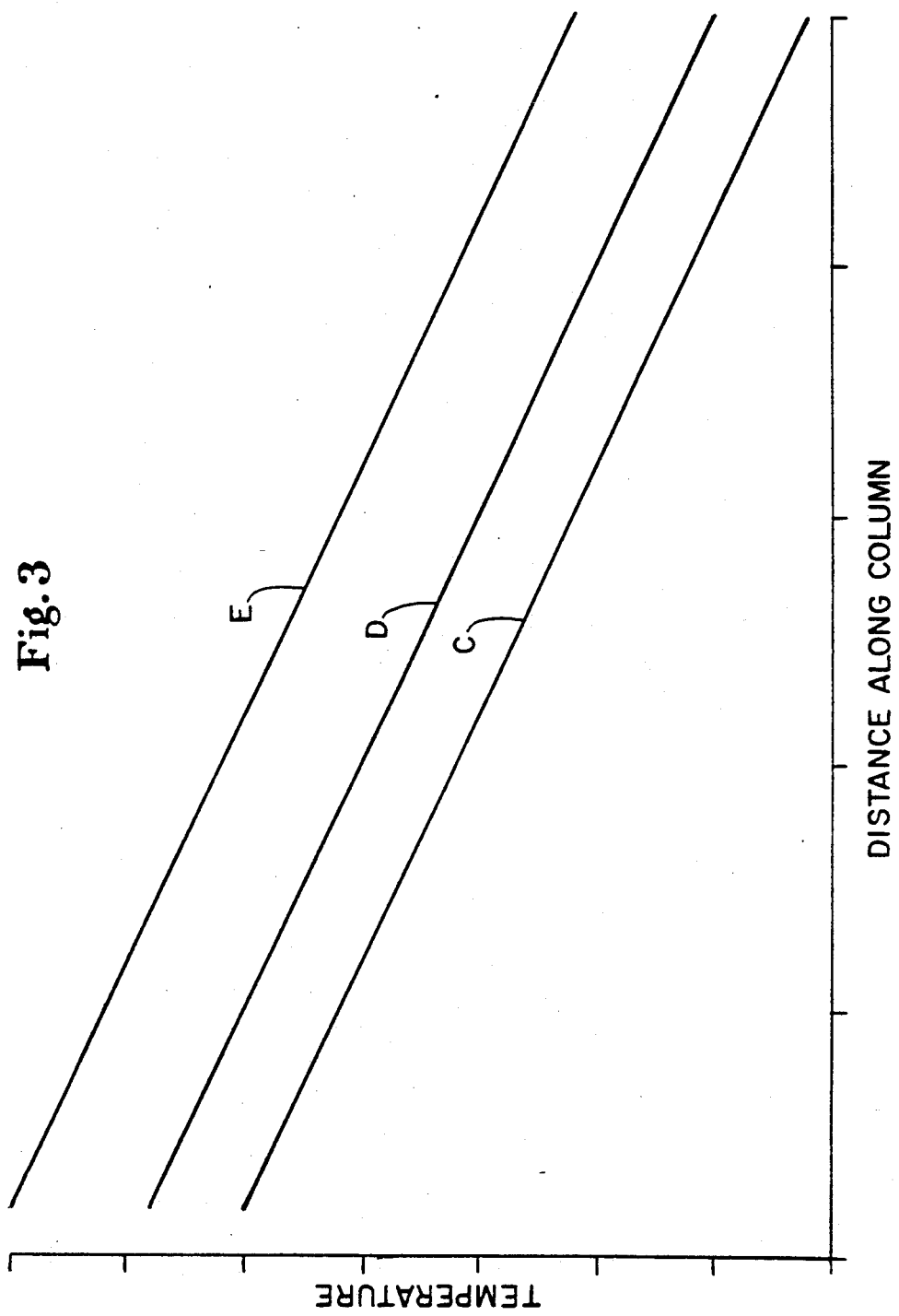
FIG. 3 shows an exemplary time-variable temperature gradient program which can be produced by the apparatus shown in FIG. 1.

FIG. 3 shows a possible time-variable temperature gradient program that can be employed using the apparatus of FIG. 1. In this graph, the internal column temperature is plotted along the y-axis, and the distance along the longitudinal length of the column is plotted on the x-axis. These plots are only exemplary, and thus no scale is shown for either axis.

The first line C of the plot in FIG. 3 shows the temperature profile in the column at time zero (the point n time when the sample is injected onto the column). After sample injection, the temperatures and/or flow rates of both the inner and outer heat transfer fluids are gradually increased, and second line D shows the temperature profile at some later point in time. This process is continued, and line E shows the temperature profile at an even later point in time.

The actual temperature gradient program employed can be tailored for the specific sample being analyzed, and the slopes and rate of change of the temperature gradient can be adjusted to nearly any desired configuration. Thus, it will be understood that the apparatus of the present invention can greatly improve the sensitivity and speed of chromatographic analysis. Should it be desired, the temperature gradient could even be inverted so that the column temperature increases along its length.

Another advantage of the apparatus and method of the present invention is that the slope of the temperature gradient can easily be varied with time, and the temperature in the column can even be returned to an isothermal condition in order to stop the movement of component bands for some period of time. In this fashion some components may be held in the column until their further migration is desired. Thus, it will be understood that the apparatus and method of the present invention provide great flexibility in the type of gradient program utilized.

The apparatus of FIG. 1 can also be applied to only a small portion of the column, if desired. For example, a temperature gradient could be established in a small portion of the column just before the detector in order to improve the resolution between peaks. Alternatively, or additionally, the apparatus could be applied to a small portion of the column right after the injection port, or even to a retention gap (a section of column which has no stationary phase). It would even be possible to simultaneously utilize three separate apparatuses: one right after the injection port, one along a portion of the length of the column, and one just before the detector. The apparatus of the invention can be used for analytical, preparative or process scale operations.

Yet another advantage of the apparatus shown in FIG. 1 is that it is readily susceptible to automatic control. Thus, heater control lines 46 and 47 are shown extending from adjustable heaters 42 and 43, respectively, and valve control lines 48 and 49 are shown extending from valves 44 and 45. Additionally, thermocouples 50 and 51 can be inserted near the entrance and exit of column 1, respectively, so that the column inlet and outlet temperature can be monitored. Further, thermocouples 52 and 53 can be inserted into the fluid inlets of the inner and outer tubular members respectively. Most preferably, the thermocouples 52 and 53 are positioned as close to the heaters 42 and 43 as possible.

Figure 4:
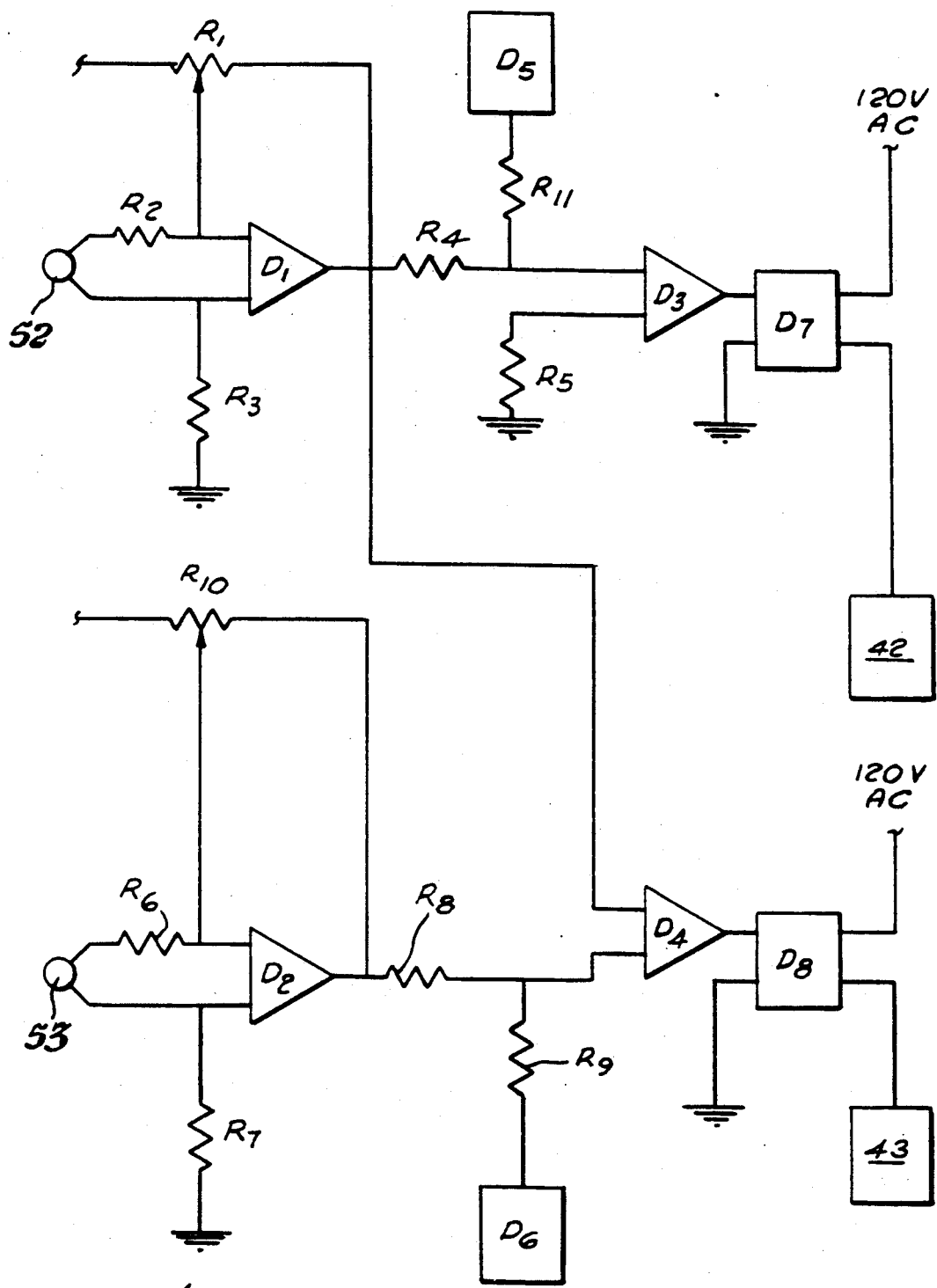
FIG. 4 is an electronic schematic drawing of a heater control circuit for controlling the heaters of the apparatus shown in FIG. 1.

Referring now to FIG. 4, therein is shown an electronic schematic drawing of a heater control circuit for controlling the heater 42 and the heater 43 of FIG. 1 via input from the thermocouple 52 and the thermocouple 53 of FIG. 1. $R_1$ and $R_{10}$ are 100,000 ohm variable resistors. $R_2$ and $R_6$ are 270 ohm resistors. $R_3$, $R_4$, $R_5$, $R_7$, $R_8$, $R_9$, and $R_{11}$ are resistors. $D_1$, $D_2$, $D_3$, and $D_4$ are type 7 operational amplifiers. $D_5$ and $D_6$ are Opto 22 brand digital to analog converters. $D_7$ and $D_8$ are Opto 22 brand solid state relays. A digital input to the converter $D_6$ controls the temperature difference between the heater 42 and the heater 43. A digital input to the converter $D_5$ controls the temperature of the heater 42.

A further advantage of the apparatus and method of the present invention is that the long recycle times experienced with temperature programming ovens can be reduced. If a steady-state temperature gradient is employed, it is evident that no recycling at all will be needed. When the temperature gradient is varied with time, the recycle time will be reduced since it is generally easier to equilibrate temperatures with a moving heat transfer fluid such as that employed. In other words, the temperature gradient of the column can be quickly returned to its desired starting profile.

The subject of this paragraph is a brief discussion of conventional capillary gas chromatography with special emphasis placed on the optimum carrier gas velocity. A carrier gas is flowed through a capillary gas chromatography column to a detector. A sample containing components of interest is introduced into the inlet end of the column. The components of interest ideally then emerge, chromatographically resolved from each other, from the outlet end of the column and are carried to the detector. The chromatographic resolution is best at the optimum carrier gas velocity. This is often referred to as the minimum in the Van Deemter plot of carrier gas velocity v. height equivalent per theoretical plate of the column. At both higher and lower carrier gas velocity, the chromatographic resolution is poorer. The optimum carrier gas velocity for any given capillary gas chromatography system must be determined by experimentation. However, for many wall coated open tubular capillary columns the optimum carrier gas velocity when helium is the carrier gas is about twenty one centimeters per second.

An important aspect of the instant invention is an improved capillary gas chromatography method of the conventional type discussed in the preceding paragraph. The improvement involves two steps. The first step is to establish a negative temperature gradient along at least a portion of the longitudinal length of the capillary gas chromatography column. One way of doing this is discussed above in reference to FIGS. 1-4. However, this way of establishing the negative temperature gradient is no critical in the method aspect of the instant invention. The second step is to flow the carrier gas through the capillary gas chromatography column at less than the optimum carrier gas velocity, i.e, at less than the optimum carrier gas velocity as determined in a conventional gas chromatography system as discussed in the preceding paragraph. The degree of the reduction in carrier gas velocity can be less than ninety, eighty, sixty, forty or twenty percent of the optimum carrier gas velocity. When using helium with many capillary columns this corresponds to less than about nineteen, seventeen, thirteen, eight or four centimeters per second. It is not presently known how low the velocity of the carrier gas can be flowed in the invention without seeing an increase in the height equivalent per theoretical plate. At some point it is believed that an increase will be seen. Presently, it is known that with a conventional wall coated open tubular capillary column and helium carrier gas in the present invention, that even at about five centimeters per second velocity of the carrier gas the height equivalent per theoretical plate has not yet started to increase.

The reduction of the height equivalent per theoretical plate at fractions of the conventional optimum carrier gas velocity has a number of benefits including the following. First, the chromatographic resolution is increased. Second, the pressure drop through the column is reduced allowing, if desired, longer columns to be used or columns having smaller internal diameters. Longer columns result in better chromatographic resolution. Columns having smaller internal diameters result in better chromatographic resolution. A slower carrier gas velocity will make the use of an FTIR detector much more practical because there can be more time to do the detection. A lower pressure drop through the column would make an unisolated membrane sample introduction system more practical.

EXAMPLE 1

An apparatus according to FIG. 1 is constructed. A length of ¼" 316 stainless steel is inserted into a slightly shorter length of ⅜" 316 stainless steel tubing so that the ¼" tubing extends beyond both ends of the ⅜" tubing. An identical set of tubings is prepared in the same manner. Next, the two sets of tubings are both wound on a lathe to produce identical coils of approximately 12" in diameter. A capillary column is inserted into both of the ¼" tubings, and the two coils are then connected to each other by means of two teflon tubings linking the ¼" and ⅜" tubings to their counterparts. The sole reason for constructing the apparatus in this fashion is to enable the column to be easily inserted into both coils. Thus, the capillary column is surrounded along nearly its entire length by a ¼" tubular member, which is in turn surrounded along nearly its entire length by a ⅜" tubular member.

The column employed is 6 meters long, and has an internal diameter of 0.53 mm. The stationary phase employed is dimethyl-polysiloxane, and the film thickness is 1 μm.

The fluid inlet and outlet for the ⅜" tubing are constructed by attaching Swagelok tee fittings (manufactured by the Crawford Fitting Co.), each having a reducing end, to each end of the ⅜" tubing. The reducing end is able to form a seal against the outer surface of the ¼" tubing. The fluid inlet and outlet for the ¼" tubing are constructed in a similar fashion using Swagelok fittings having reducing ends which seal against the surface of the capillary column. One end of the capillary column is connected to a GC injection port, and a helium gas supply source. The Swagelok fitting nearest the injection port on the ¼" tubing is connected to a heater and an air supply, so that heated air can be flowed through the ¼" tubing in the same direction as the carrier gas flow. A needle valve is connected to the inlet of the heater in order to control the air flow rate. The Swagelok fitting nearest the detector on the ⅜" tubing is also connected to a heater and an air supply source, so that heated air can be flowed through the ⅜" tubing in the opposite direction of the carrier gas flow. A thermocouple is then inserted into the exit of the column and is fed along the entire length of the column to a point approximately 2 feet from the injection port.

The air supply to the inner tubular member is actuated and the needle valve opened to permit air to flow. The air is then heated to approximately 55° C. No air is permitted to flow through the outer tubular member. The temperature in the column as measured by the thermocouple is then determined. Thereafter the thermocouple is pulled through the column 12 inches at a time, and the temperature recorded. Curve B in FIG. 5, wherein temperature is plotted against the distance along the length of the column, shows the resulting nonlinear, decaying temperature gradient.

The above temperature measuring process is repeated, however this time air at a temperature of 20° C. is permitted to flow through the outer tubular member. The temperature gradient produced is shown by line A of FIG. 5, and is reasonably linear along the entire length of the column.

EXAMPLE 2

The identical column used in Example 1 above is placed in a traditional gas chromatography apparatus, i.e., a Hewlett Packard HP5890 gas chromatograph. A splitless injection port is utilized, along with a flame ionization detector. The injector temperature is 250° C., and helium flowing at 9 cc/min is utilized as the carrier gas. The detector temperature is also 250° C. The sample mixture contained pentane ($C_5$), hexane ($C_6$), heptane ($C_7$), octane ($C_8$), and nonane ($C_9$).

Figure 6:
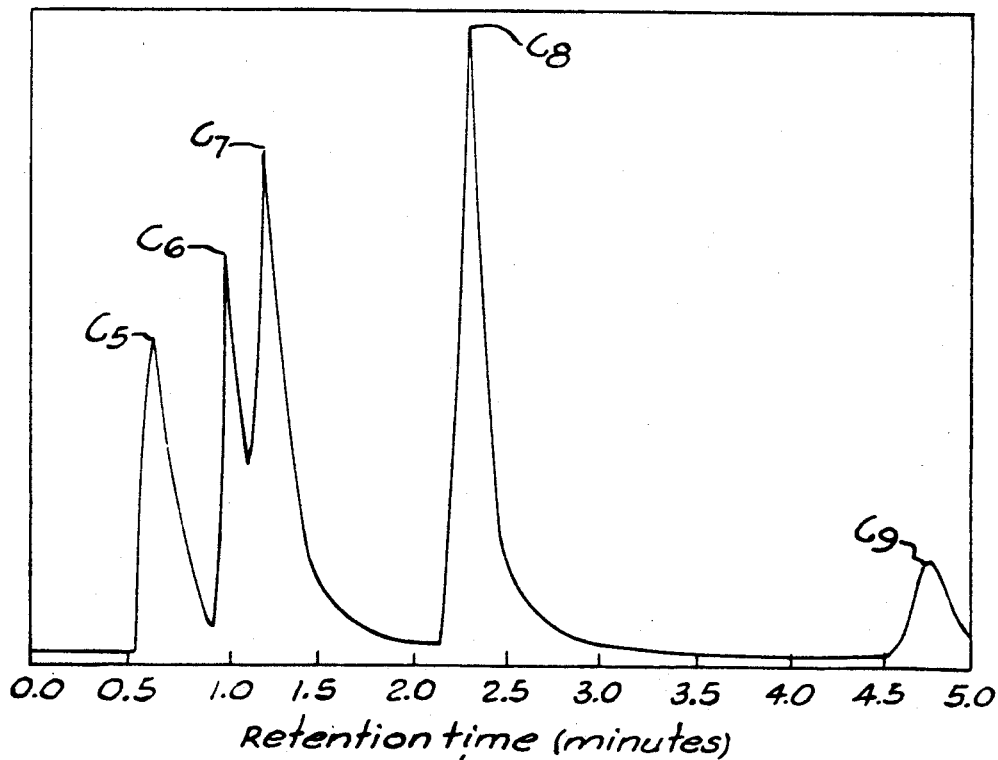
FIG. 6 is a chromatogram from an isothermal analysis of a hydrocarbon sample utilizing standard chromatography equipment wherein the column temperature is 50° C.

FIG. 6 shows the resulting chromatogram obtained from an isothermal analysis at 50° C. of a sample of the above mixture.

Figure 5:
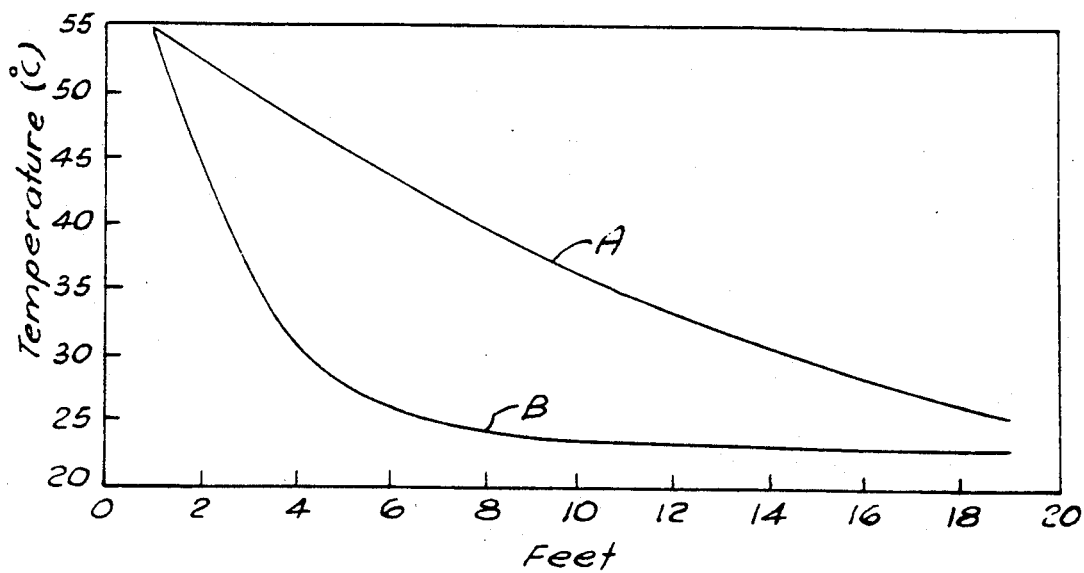
FIG. 5 shows steady-state temperature profiles in a chromatography column comparing the preferred countercurrent flow and a singular heat transfer fluid flow, utilizing the apparatus of FIG. 1.
Figure 7:
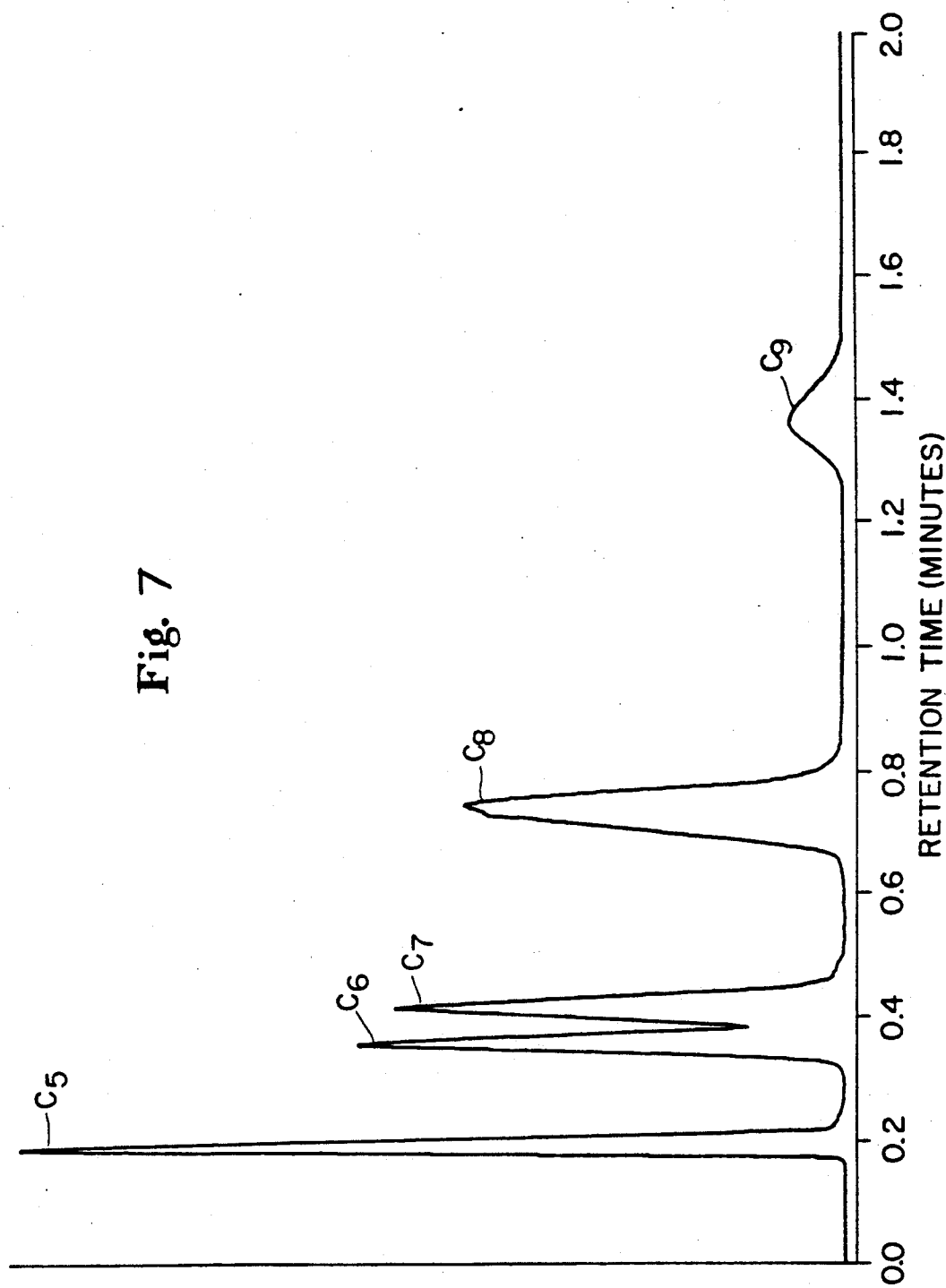
FIG. 7 is a chromatogram of a steady-state temperature gradient analysis, utilizing the apparatus shown in FIG. 1, and the same column as FIG. 6, of a sample of the same solution from FIG. 6 wherein the column temperature gradient was from 150° C. near the column entrance, to 50° C. near the column outlet.

Next, a sample of the same mixture used in FIG. 6 is analyzed using the apparatus of Example 1, above. Countercurrent heat transfer fluid flow was utilized, and a temperature gradient similar to line A of FIG. 5 is established in the column. The temperature of the inner and outer heat transfer fluids are adjusted so that a steady-state, linear temperature gradient of negative slope, ranging from about 150° C. to about 50° C., is established along the length of the capillary column. Carrier gas type, carrier gas flow rate, column, injection temperature, detector type and detector temperature are all identical to those used to create FIG. 6 above. The resulting chromatogram is shown in FIG. 7.

What is claimed is:

1. A method for temperature gradient chromatography, comprising the steps of:
   (a) moderating the temperature of a chromatographic column with a first heat exchange fluid;
   (b) moderating the temperature of the first heat exchange fluid with a second heat exchange fluid so that a generally linear temperature gradient is created along the longitudinal length of the chromatographic column.

2. The method of claim 1 wherein the chromatographic column is a gas chromatographic column, wherein the first heat exchange fluid is a gas and wherein the second heat exchange fluid is a gas.

3. The method of claim 2 wherein the chromatographic column is an open tubular capillary gas chromatography column.

4. An improved capillary gas chromatography method of the type that generally includes the steps of flowing a carrier gas through a capillary gas chromatography column to a detector, introducing a sample to be analyzed into the column and then detecting chromatographically resolved components of interest of the sample, the method having an optimum carrier gas velocity through the column, wherein the improvement comprises the steps of:
   (a) establishing a negative temperature gradient along at least a portion of the longitudinal length of the capillary gas chromatography column;
   (b) flowing the carrier gas through the capillary gas chromatography column at less than the optimum carrier gas velocity.

5. The method of claim 4, wherein in step (b) the flow velocity of the carrier gas is less than ninety percent of the optimum carrier gas velocity.

6. The method of claim 4, wherein in step (b) the flow velocity of the carrier gas is less than eighty percent of the optimum carrier gas velocity.

7. The method of claim 4, wherein in step (b) the flow velocity of the carrier gas is less than sixty percent of the optimum carrier gas velocity.

8. The method of claim 4, wherein in step (b) the flow velocity of the carrier gas is less than forty percent of the optimum carrier gas velocity.

9. The method of claim 4, wherein in step (b) the flow velocity of the carrier gas is less than twenty percent of the optimum carrier gas velocity.

10. The method of claim 4 wherein the carrier gas is helium, wherein the capillary gas chromatography column is a wall coated open tubular capillary gas chromatography column and wherein in step (b) the flow velocity of the helium is less than twenty one centimeters per second.

11. The method of claim 4 wherein the carrier gas is helium, wherein the capillary gas chromatography column is a wall coated open tubular capillary gas chromatography column and wherein in step (b) the flow velocity of the helium is less than nineteen centimeters per second.

12. The method of claim 4 wherein the carrier gas is helium, wherein the capillary gas chromatography column is a wall coated open tubular capillary gas chromatography column and wherein in step (b) the flow velocity of the helium is less than seventeen centimeters per second.

13. The method of claim 4 wherein the carrier gas is helium, wherein the capillary gas chromatography column is a wall coated open tubular capillary gas chromatography column and wherein in step (b) the flow velocity of the helium is less than thirteen centimeters per second.

14. The method of claim 4 wherein the carrier gas is helium, wherein the capillary gas chromatography column is a wall coated open tubular capillary gas chromatography column and wherein in step (b) the flow velocity of the helium is less than eight centimeters per second.

15. The method of claim 4 wherein the carrier gas is helium, wherein the capillary gas chromatography column is a wall coated open tubular capillary gas chromatography column and wherein in step (b) the flow velocity of the helium is less than four centimeters per second.

16. The method of claim 4 wherein the capillary gas chromatography column is an open tubular capillary gas chromatography column.

17. The method of claim 16 wherein the open tubular capillary gas chromatography column is a wall coated open tubular capillary gas chromatography column.

18. Apparatus for temperature gradient chromatography, said apparatus comprising:
  (a) an inner tubular member surrounding, and extending along at least a portion of the longitudinal length of a chromatography column;
  (b) an outer tubular member surrounding, and extending along at least a portion of the longitudinal length of the inner tubular member;
  (c) means for flowing an inner heat transfer fluid between the inner tubular member and the column; and
  (d) means for flowing an outer heat transfer fluid between the outer tubular member and the inner tubular member.

19. The apparatus of claim 18 further comprising means for heating the inner heat transfer fluid.

20. The apparatus of claim 19, further comprising means for heating the outer heat transfer fluid.

* * * * *